(12) United States Patent
Malek

(10) Patent No.: US 7,935,133 B2
(45) Date of Patent: May 3, 2011

(54) INTERLAMINAR HOOK

(75) Inventor: Michel H. Malek, Chicago, IL (US)

(73) Assignee: MMSN Limited Partnership, Kankakee, IL (US)

( * ) Notice: Subject to any disclaimer, the term of this patent is extended or adjusted under 35 U.S.C. 154(b) by 178 days.

(21) Appl. No.: 12/028,343

(22) Filed: Feb. 8, 2008

(65) Prior Publication Data

US 2009/0204149 A1    Aug. 13, 2009

(51) Int. Cl.
*A61B 17/70*    (2006.01)

(52) U.S. Cl. ...... 606/249; 606/246; 606/276; 623/17.11

(58) Field of Classification Search .......... 606/246–249, 606/264–279, 60, 61; 623/17.11–17.16
See application file for complete search history.

(56) References Cited

U.S. PATENT DOCUMENTS

| | | |
|---|---|---|
| 4,011,602 A | 3/1977 | Rybicki et al. |
| 4,349,921 A | 9/1982 | Kuntz |
| 4,401,112 A | 8/1983 | Resaian |
| 4,643,178 A | 2/1987 | Nastari et al. |
| 4,657,550 A | 4/1987 | Daher |
| 4,743,256 A | 5/1988 | Brantigan |
| 4,743,260 A | 5/1988 | Burton |
| 4,759,766 A | 7/1988 | Büettner-Janz et al. |
| 4,759,769 A | 7/1988 | Hedman et al. |
| 4,863,476 A | 9/1989 | Shepperd |
| 4,946,378 A | 8/1990 | Hirayama et al. |
| 4,946,458 A | 8/1990 | Harms et al. |
| 4,997,432 A | 3/1991 | Keller |
| 5,024,670 A | 6/1991 | Smith et al. |
| 5,084,048 A | 1/1992 | Jacob et al. |
| 5,092,866 A | 3/1992 | Breard et al. |
| 5,122,130 A | 6/1992 | Keller |
| 5,246,458 A | 9/1993 | Graham |
| 5,258,031 A | 11/1993 | Salib et al. |
| 5,261,911 A | 11/1993 | Carl |
| 5,282,863 A | 2/1994 | Burton |
| 5,306,310 A | 4/1994 | Siebels |
| 5,314,477 A | 5/1994 | Marnay |
| 5,314,478 A | 5/1994 | Oka et al. |
| 5,336,223 A | 8/1994 | Rogers |
| 5,352,224 A | 10/1994 | Westermann |

(Continued)

FOREIGN PATENT DOCUMENTS

DE    22 63 842 A    7/1974

(Continued)

OTHER PUBLICATIONS

International Search Report and Written Opinion for PCT International Application No. PCT/US2009/033057 dated Mar. 10, 2009.

(Continued)

*Primary Examiner* — Eduardo C Robert
*Assistant Examiner* — Christina Negrelli
(74) *Attorney, Agent, or Firm* — Foley & Lardner LLP

(57) ABSTRACT

A medical apparatus for alleviating the symptoms associated with spinal stenosis have a body including first and second supports disposed along the length of the body. The first support is configured to accommodate at least a portion of a vertebral component of a first vertebra disposed above or below a second vertebra. The second support is configured to accommodate at least a portion of a vertebral component of the second vertebra. The distance between the supports is sufficient to increase the space between the first vertebra and the second vertebra. Methods for using the apparatus include implanting the apparatus into a subject.

27 Claims, 5 Drawing Sheets

U.S. PATENT DOCUMENTS

| | | |
|---|---|---|
| 5,375,823 A | 12/1994 | Navas |
| 5,380,324 A | 1/1995 | Müller et al. |
| 5,380,328 A | 1/1995 | Morgan |
| 5,401,269 A | 3/1995 | Büttner-Janz et al. |
| 5,415,659 A * | 5/1995 | Lee et al. ................. 606/276 |
| 5,437,671 A | 8/1995 | Lozier et al. |
| 5,458,641 A | 10/1995 | Ramirez Jimenez |
| 5,496,318 A | 3/1996 | Howland et al. |
| 5,534,029 A | 7/1996 | Shima |
| 5,536,124 A | 7/1996 | Silva |
| 5,540,688 A | 7/1996 | Navas |
| 5,556,431 A | 9/1996 | Büttner-Janz |
| 5,562,738 A | 10/1996 | Boyd et al. |
| 5,591,166 A | 1/1997 | Bernhardt et al. |
| 5,607,425 A | 3/1997 | Rogozinski |
| 5,628,740 A | 5/1997 | Mullane |
| 5,645,596 A | 7/1997 | Kim et al. |
| 5,649,925 A | 7/1997 | Barbera Alacreu |
| 5,672,175 A | 9/1997 | Martin |
| 5,688,275 A | 11/1997 | Koros et al. |
| 5,702,453 A | 12/1997 | Rabbe et al. |
| 5,702,455 A | 12/1997 | Saggar |
| 5,713,899 A | 2/1998 | Marnay et al. |
| 5,725,582 A | 3/1998 | Bevan et al. |
| 5,776,198 A | 7/1998 | Rabbe et al. |
| 5,836,948 A | 11/1998 | Zucherman et al. |
| 5,888,226 A | 3/1999 | Rogozinski |
| 5,893,889 A | 4/1999 | Harrington |
| 5,951,553 A | 9/1999 | Betz et al. |
| 5,989,290 A | 11/1999 | Biedermann et al. |
| 6,019,792 A | 2/2000 | Cauthen |
| 6,030,389 A | 2/2000 | Wagner et al. |
| 6,063,121 A | 5/2000 | Xavier et al. |
| 6,074,390 A | 6/2000 | Zucherman et al. |
| 6,083,224 A | 7/2000 | Gertzbein et al. |
| 6,113,637 A | 9/2000 | Gill et al. |
| 6,139,579 A | 10/2000 | Steffee et al. |
| 6,146,421 A | 11/2000 | Gordon et al. |
| 6,179,874 B1 | 1/2001 | Cauthen |
| 6,214,012 B1 | 4/2001 | Karpman et al. |
| 6,217,578 B1 | 4/2001 | Crozet et al. |
| 6,228,118 B1 | 5/2001 | Gordon |
| 6,241,730 B1 | 6/2001 | Alby |
| 6,293,949 B1 | 9/2001 | Justis et al. |
| 6,296,644 B1 | 10/2001 | Saurat et al. |
| 6,296,664 B1 | 10/2001 | Middleton |
| 6,315,797 B1 | 11/2001 | Middleton |
| 6,368,350 B1 | 4/2002 | Erickson et al. |
| 6,375,682 B1 | 4/2002 | Fleischmann et al. |
| 6,375,683 B1 | 4/2002 | Crozet et al. |
| 6,395,034 B1 | 5/2002 | Suddaby |
| 6,402,750 B1 | 6/2002 | Atkinson et al. |
| 6,419,703 B1 | 7/2002 | Fallin et al. |
| 6,454,807 B1 | 9/2002 | Jackson |
| 6,478,800 B1 | 11/2002 | Fraser et al. |
| 6,500,178 B2 | 12/2002 | Zucherman et al. |
| 6,517,580 B1 | 2/2003 | Ramadan et al. |
| 6,520,990 B1 | 2/2003 | Ray |
| 6,540,785 B1 | 4/2003 | Gill et al. |
| 6,554,831 B1 | 4/2003 | Rivard et al. |
| 6,565,605 B2 | 5/2003 | Goble et al. |
| 6,579,319 B2 | 6/2003 | Goble et al. |
| 6,579,320 B1 | 6/2003 | Gauchet et al. |
| 6,582,466 B1 | 6/2003 | Gauchet |
| 6,582,468 B1 | 6/2003 | Gauchet |
| 6,585,769 B1 | 7/2003 | Muhanna et al. |
| 6,607,558 B2 | 8/2003 | Kuras |
| 6,616,669 B2 | 9/2003 | Ogilvie et al. |
| 6,626,905 B1 | 9/2003 | Schmiel et al. |
| 6,626,908 B2 | 9/2003 | Cooper et al. |
| 6,652,585 B2 | 11/2003 | Lange |
| 6,685,742 B1 | 2/2004 | Jackson |
| 6,695,842 B2 | 2/2004 | Zucherman et al. |
| 6,730,126 B2 | 5/2004 | Boehm et al. |
| 6,752,831 B2 | 6/2004 | Sybert et al. |
| 6,761,720 B1 | 7/2004 | Senegas |
| 6,764,515 B2 | 7/2004 | Ralph et al. |
| 6,835,205 B2 | 12/2004 | Atkinson et al. |
| 6,852,128 B2 | 2/2005 | Lange |
| 6,902,566 B2 | 6/2005 | Zucherman et al. |
| 6,946,000 B2 | 9/2005 | Senegas et al. |
| 6,966,910 B2 | 11/2005 | Ritland |
| 6,966,931 B2 | 11/2005 | Huang |
| 6,989,011 B2 | 1/2006 | Paul et al. |
| 7,022,138 B2 | 4/2006 | Mashburn |
| 7,025,787 B2 | 4/2006 | Bryan et al. |
| 7,041,138 B2 | 5/2006 | Lange |
| 7,044,970 B2 | 5/2006 | Errico et al. |
| 7,056,343 B2 | 6/2006 | Schafer et al. |
| 7,101,375 B2 | 9/2006 | Zucherman et al. |
| 7,147,665 B1 | 12/2006 | Bryan et al. |
| 7,175,623 B2 | 2/2007 | Thramann et al. |
| 7,186,256 B2 | 3/2007 | Michelson |
| 7,201,751 B2 | 4/2007 | Zucherman et al. |
| 7,255,713 B2 | 8/2007 | Malek |
| 7,282,064 B2 | 10/2007 | Chin |
| 7,318,825 B2 | 1/2008 | Butler et al. |
| 7,402,176 B2 | 7/2008 | Malek |
| 2001/0016773 A1 | 8/2001 | Serhan et al. |
| 2001/0029375 A1 * | 10/2001 | Betz et al. ................. 606/61 |
| 2001/0032020 A1 | 10/2001 | Besselink |
| 2001/0037111 A1 | 11/2001 | Dixon et al. |
| 2001/0051829 A1 | 12/2001 | Middleton |
| 2002/0022888 A1 | 2/2002 | Serhan et al. |
| 2002/0107574 A1 | 8/2002 | Boehm, Jr. et al. |
| 2002/0111683 A1 | 8/2002 | Ralph et al. |
| 2002/0147454 A1 | 10/2002 | Neto |
| 2003/0009223 A1 | 1/2003 | Fehling et al. |
| 2003/0009226 A1 | 1/2003 | Graf |
| 2003/0018390 A1 | 1/2003 | Husson |
| 2003/0023312 A1 | 1/2003 | Thalgott |
| 2003/0032958 A1 | 2/2003 | Soubeiran |
| 2003/0055427 A1 | 3/2003 | Graf |
| 2003/0100951 A1 | 5/2003 | Serhan et al. |
| 2003/0176861 A1 | 9/2003 | Reed |
| 2003/0191534 A1 | 10/2003 | Viart et al. |
| 2003/0229348 A1 | 12/2003 | Sevrain |
| 2004/0002762 A1 | 1/2004 | Hawkins |
| 2004/0153156 A1 | 8/2004 | Cohen et al. |
| 2004/0167626 A1 | 8/2004 | Geremakis et al. |
| 2005/0085910 A1 | 4/2005 | Sweeney |
| 2005/0113927 A1 | 5/2005 | Malek |
| 2005/0143823 A1 | 6/2005 | Boyd et al. |
| 2005/0165486 A1 | 7/2005 | Trieu |
| 2005/0209593 A1 | 9/2005 | Kolb |
| 2005/0209697 A1 | 9/2005 | Paponneau et al. |
| 2005/0234425 A1 | 10/2005 | Miller et al. |
| 2006/0036243 A1 * | 2/2006 | Sasso et al. ................. 606/61 |
| 2006/0079895 A1 | 4/2006 | McLeer |
| 2006/0106381 A1 | 5/2006 | Ferree et al. |
| 2006/0161154 A1 | 7/2006 | McAfee |
| 2006/0200140 A1 | 9/2006 | Lange |
| 2006/0224223 A1 | 10/2006 | Podhajsky et al. |
| 2006/0235390 A1 * | 10/2006 | Zhang et al. ................. 606/61 |
| 2007/0010813 A1 * | 1/2007 | Zucherman et al. ........... 606/61 |
| 2007/0112299 A1 | 5/2007 | Smit et al. |
| 2007/0173937 A1 | 7/2007 | Khalili |
| 2007/0270828 A1 | 11/2007 | Bruneau et al. |
| 2008/0027444 A1 | 1/2008 | Malek |
| 2009/0062919 A1 | 3/2009 | Malek |
| 2009/0177233 A1 | 7/2009 | Malek |
| 2009/0204149 A1 | 8/2009 | Malek |
| 2009/0287118 A1 | 11/2009 | Malek |
| 2010/0121378 A1 | 5/2010 | Malek |
| 2010/0160964 A1 | 6/2010 | Malek |

FOREIGN PATENT DOCUMENTS

| | | |
|---|---|---|
| DE | 30 23 353 A1 | 4/1981 |
| EP | 0 176 728 A | 4/1986 |
| EP | 0 560 140 B1 | 9/1993 |
| EP | 0 560 141 A | 9/1993 |
| EP | 0 566 810 B1 | 10/1993 |
| FR | 2 694 882 A | 2/1994 |
| FR | 2 801 782 | 12/1999 |
| FR | 2 805 985 | 9/2001 |
| WO | WO 94/04100 | 3/1994 |
| WO | WO 95/26697 | 10/1995 |

| WO | WO 01/06939 | 2/2001 |
| WO | WO 02/24087 | 3/2002 |
| WO | WO 2008/014337 | 1/2008 |
| WO | WO 2009/088746 | 7/2009 |
| WO | WO 2009/100117 | 8/2009 |

OTHER PUBLICATIONS

"New Device Approval—X STOP® Interspinous Process Decompression System (XSTOP)—P040001," U.S. Food and Drug Administration, http://www.fda.gov/cdrh/mda/docs/p040001.html; printed Apr. 18, 2007.

The International Search Report and Written Opinion for PCT/US2004/032116 mailed on Feb. 16, 2005, 12 pages.

"Anatomic Facet Replacement System (AFRS™)," *Natural Motion*; published by Facet Solutions, Inc.; http://www.facetsolutions.com/Device.html on or before Nov. 2, 2007, 1 page.

* cited by examiner

INTERLAMINAR HOOK

FIELD OF THE INVENTION

The invention generally relates to medical apparatuses for the spine. More specifically, medical apparatuses and methods are disclosed which are capable of increasing the space between adjacent vertebrae, thereby alleviating the symptoms of spinal stenosis.

BACKGROUND

Spinal stenosis is a spinal condition that causes a narrowing in one or more areas of the spine. The narrowing can occur at the center of the spine, in the canals branching off the spine, and/or between the vertebrae of the spine. The narrowing can put pressure on the spinal cord and/or on the nerves that branch out from the compressed areas. Similarly, the narrowing can also put pressure on, and restrict the flow of blood in blood vessels in these areas. Spinal stenosis can lead to a number of symptoms including cramping, pain, and numbness in the legs, back, neck, shoulders and arms; a loss of sensation in extremities; and even problems with bladder or bowel function.

Implantable devices that create additional space for the spinal cord, spinal nerves, and/or blood vessels may be used to treat spinal stenosis. Some devices create the necessary space by distracting the spinous processes of adjacent vertebrae. However, the spinous processes are relatively fragile and may be easily damaged, fractured, or even broken off, by devices exerting force on these vertebral components. In some cases, the softer spinous process yields to the device, leading to a recurrence of the stenosis. In other cases, the device may be reincorporated into the softer spinous process, effectively providing no benefit in reducing the symptoms of spinal stenosis.

SUMMARY

Medical apparatuses for alleviating the symptoms associated with spinal stenosis and methods for using the apparatuses are provided herein. The apparatuses are capable of increasing the space between vertebrae, thereby relieving the pressure on the spinal cord, spinal nerves, and/or blood vessels. The apparatuses create the necessary space by distracting a variety of vertebral components, including laminae.

In one aspect, the medical apparatus comprises a body. The body may take a variety of forms. Similarly, the placement of the body relative to the spine may vary. The body of the apparatus also comprises a first support and a second support disposed along the length of the body. The first support is configured to accommodate at least a portion of a vertebral component of a first vertebra disposed above or below a second vertebra and the second support is configured to accommodate at least a portion of a vertebral component of the second vertebra. The first and second supports may be configured to accommodate a; variety of vertebral components, including laminae. In some aspects, the first support and the second support are configured to accommodate at least a portion of the superior edge or the inferior edge of the lamina. The relative distance between the first and second supports may vary. In one aspect, the distance is sufficient to increase the space between the first vertebra and the second vertebra.

The first and second supports may take a variety of shapes and forms. In one aspect, the first support is a hook. In another aspect, both the first and second supports are hooks. In other aspects, the second support comprises at least two pegs extending from an end of the body to form a V-shape. In still another aspect, the second support comprises three pegs extending from an end of the body to form a tripod or claw shape. In a further aspect, the first support is a hook and the second support comprises at least two pegs extending from an end of the body to form a V-shape.

The dimensions and materials used to form the body and the first and second supports may vary. In one aspect, the body, the first support, and the second support comprise a biologically compatible material selected from the group consisting of titanium, a titanium alloy, stainless steel, and a polymer.

The medical apparatus may further comprise an arm extending from the body of the apparatus. The arm may be attached to the body in various ways. In one aspect, the arm comprises an aperture adapted to receive the body. The orientation of the arm relative to the body may vary. In one aspect, the arm extends from, and is substantially perpendicular to the body. The shape, dimensions and materials used to form the arm may vary. In one aspect, the arm further comprises a sleeve. The cross-section of the sleeve may vary. In one aspect, the cross-section is in the shape of an ellipse or an egg. Finally, the placement of the arm relative to the spine may vary.

The medical apparatus may further comprise a wing extending from the arm of the apparatus. The wing may be attached to the arm in various ways and in various positions and orientations. Similarly, the placement of the wing relative to the spine may vary. Finally, the shape, dimensions, and materials used to form the wing may vary.

The medical apparatuses may be used without fixing, attaching or otherwise securing the apparatus to the spine. In other aspects, the apparatuses may be secured to the spine in various ways.

In another aspect, methods of using the medical apparatuses are provided. The methods comprise implanting into a subject any of the apparatuses disclosed herein. In one aspect, the methods comprise implanting into a subject a medical apparatus comprising a body, wherein the body comprises a first support and a second support disposed along the length of the body. The first support is configured to accommodate at least a portion of a lamina of a first vertebra disposed above or below a second vertebra and the second support is configured to accommodate at least a portion of a lamina of the second vertebra. The distance between the first and second supports is sufficient to increase the space between the first vertebra and the second vertebra.

In another aspect, the first support is a hook and the second support comprises at, least two pegs extending from an end of the body to form a V-shape. In yet another aspect, the apparatus further comprises an arm extending from, and substantially perpendicular to, the body, and a wing extending from, and substantially perpendicular to, the arm. In still another aspect, the method comprises implanting the apparatus by inserting the arm between the spinous process of the first vertebra and the spinous process of the second vertebra, connecting the body to the arm, and connecting the wing to the arm.

The methods may comprise other steps. In one aspect, the methods further comprise contacting the first support to at least a portion of the lamina of the first vertebra and contacting the second support to at least a portion of the lamina of the second vertebra. In another aspect, the methods further comprise distracting the first and second vertebrae prior to completion of implantation. Still other methods further comprise forming a notch in the lamina of the first vertebra or in the lamina of the second vertebra or both, wherein the notch is configured to accommodate the first support or the second support.

DETAILED DESCRIPTION

Figure 1A:
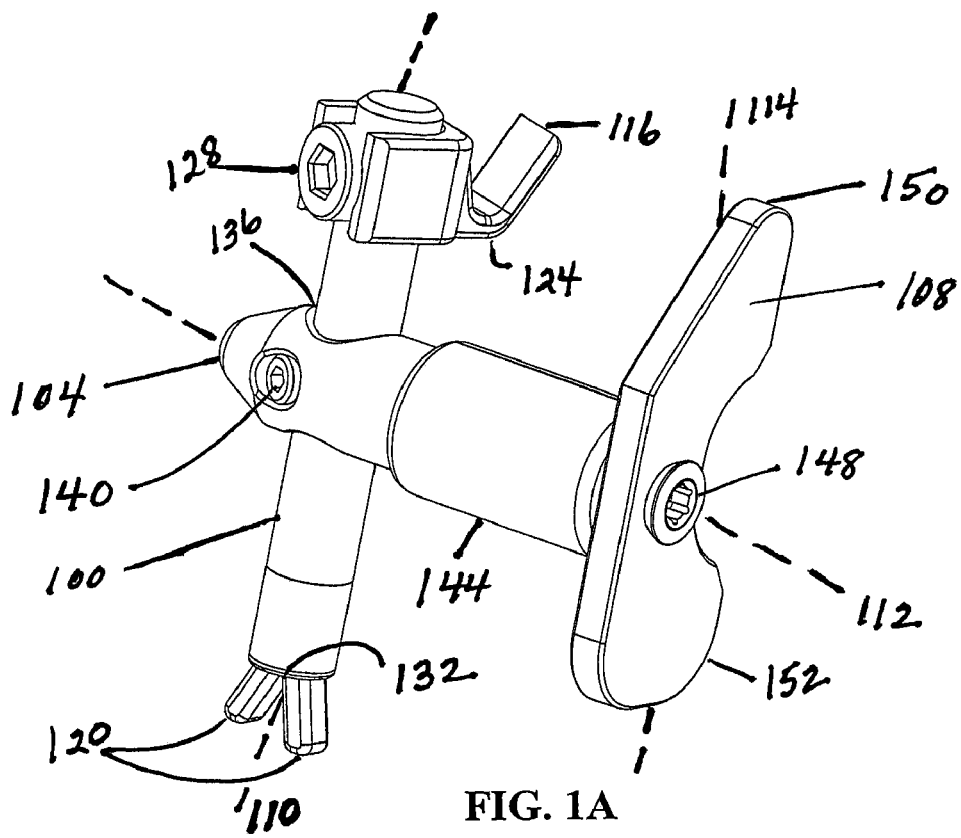
FIG. 1A is an illustration of an interlaminar hook apparatus according to one embodiment.

Medical apparatuses for alleviating the symptoms associated with spinal stenosis and methods for using the apparatuses are provided herein. The apparatuses are capable of increasing the space between vertebrae, thereby relieving the pressure on the spinal cord, spinal nerves, and/or blood vessels. The apparatuses can be used to introduce space at one level or more than one level in the cervical, thoracic and lumbar regions of the spine. The apparatuses may find use in combination with other procedures, such as a full or partial laminectomy.

In one aspect, a medical apparatus comprise a body. The body may take a variety of forms, including, but not limited to, a rod, bar, or plate. In some embodiments, the body is a rigid rod. In other embodiments, the body is semi-rigid. For example, the body may comprise a plurality of rods connected together by joints. Suitable joints include, but are not limited to any of the joints described in U.S. Patent Publication Number 2005/0113927.

When implanted, the exact placement of the body relative to the spine may vary. Generally, the body is positioned at posterior location. In some embodiments, the body is positioned along the longitudinal axis of the spine. In other embodiments, the body is positioned off-axis. In such embodiments, the body is positioned to either side of the spinous processes that run along the axis of the spine. The longitudinal axis of the body is generally aligned with the longitudinal axis of the spine, although non-parallel alignments are within the scope of the invention.

The body of the apparatus comprises two opposing supports disposed along the length of the body. The first support is configured to accommodate a vertebral component of a first vertebra disposed above or below a second vertebra. One or more other vertebrae may be disposed between the first and second vertebrae. The second support is configured to accommodate a vertebral component of the second vertebra. The supports may accommodate a variety of vertebral components, including, but not limited to a spinous process, lamina, and an articular process. In some embodiments, the supports are configured to accommodated at least a portion of a lamina. In other embodiments, the supports are configured to accommodate at, least a portion of the superior edge of a lamina or the inferior edge of a lamina. In yet other embodiments, the supports are configured to accommodate at least a portion of the area on a vertebra where the lamina and spinous process merge. This area may be located at the superior aspect of the lamina and spinous process, or at the inferior aspect of the lamina and spinous process.

A variety of supports may be used with the apparatuses. In some embodiments, the support is a hook. The bend in the hook can be placed over a variety of vertebral components, as described above. Alternatively, these vertebral components may rest in, and be supported by, the bend in the hook. In other embodiments the support comprises at least two pegs extending from an end of the body to form a V-shape. In still other embodiments, the support comprises three pegs extending from the end of the body to form a tripod or claw shape. The vertex formed by the V-shaped pegs or tripod (claw)-shaped pegs can be placed over a variety of vertebral components, as described above. Alternatively, these vertebral components may rest in, and be supported by, the vertex.

The relative distance between the first and second supports, and thus the length of the body, may vary. The distance generally depends upon the amount of space to be introduced between vertebrae. By way of a non-limiting example, a vertebral component of a first vertebra is supported by the first support and the second support is placed over a vertebral component of a second vertebra disposed below the first vertebra. Increasing the distance between, the supports forces the vertebrae apart, thereby increasing the space between the vertebrae. In some embodiments, the distance is sufficient to distract and increase the space between vertebrae beyond the normal, physiologic space between the vertebrae. Ire other embodiments, the distance is sufficient to reduce the symptoms associated with spinal stenosis.

The exact dimensions of the supports may vary, depending upon considerations such as minimizing interference with elements of the spinal column, providing a stable surface upon which to support, or place over, vertebral components, and evenly distributing the load between the vertebral components and the supports. The supports may be attached to the body of the apparatus in a variety of ways, including, but not limited to screws, pins, welds, clips, snaps and the like. The supports may comprise a connector for attaching the support to the body, including, but not limited to screws, pins, clips, snaps and the like.

In some embodiments, the apparatuses may further comprise an arm extending from the body of the apparatus. The arm may be attached to the body of the apparatus in a variety of ways and may comprise a variety of connectors for attaching the arm to the body as described above. The arm may further comprise an aperture configured to receive the body of the apparatus. The position of the arm along the body may vary. In some embodiments, the arm is positioned near the midsection of the body. Similarly, the orientation of the arm relative to the body may vary. In some embodiments, the arm is substantially perpendicular to the longitudinal axis of the body. By substantially perpendicular, it is meant that the longitudinal axis of the body and the longitudinal axis of the arm form an approximate right angle. However, angles less than or greater than 90° are also within the scope of the invention.

When implanted, the exact placement of the arm relative to the spine may also vary. Generally, the arm is positioned at posterior location. In some embodiments, the arm is positioned between adjacent spinous processes so that the longitudinal axis of the arm is substantially perpendicular to the longitudinal axis of the spine.

The exact shape of the arm may vary. The arm may take a variety of forms, including, but not limited to a rod, bar, or plate. In embodiments in which the arm is a rod, the cross-section of the rod may be a circle or some other shape. For example, the cross-section may be an elliptical shape or an egg shape. In embodiments in which the arm is, positioned between adjacent spinous processes, these shapes may serve to accommodate the shape of the interspinous process region. In embodiments in which the arm makes contact with adjacent spinous processes, these shapes serve to support a larger surface of the spinous processes and to more evenly distribute the load between the arm and the bone. In other embodiments, one or both ends of the arm may form a blunted point to help guide the arm through the spinal tissue and ligaments during implantation.

Similarly, the exact dimensions of the arm may vary. The desired length will generally depend upon the desired placement of the body relative to the spine and for those embodiments including a wing, upon the desired placement of the wing relative to the spine, as further described below. For example, the arm must be longer for those placements of the body and/or wing substantially off-center from the axis of the spine. However, the length of the arm will also depend upon considerations such as minimizing interference with other elements of the spine and ensuring the arm is easily implantable. Similarly, the width of the arm will also depend upon these considerations. In some embodiments, the arm makes no contact or only minimal contact with the spinous processes of adjacent vertebrae. However, in some embodiments, the width of the arm is sufficient to contact and spread apart the spinous processes of adjacent vertebrae.

In some embodiments, the arm is substantially straight. In other embodiments, the arm may be curved or bowed. In such embodiments, the curved or bowed arm may facilitate implantation of the apparatus and adjustment of the apparatus once implanted. The direction of the curvature or bow in the arm may vary. However, in some embodiments, the arm is curved or bowed posteriorly. In yet other embodiments, the arm may be comprised of a flexible, malleable, or elastic material so that the arm may be flexed, bent, folded, twisted, stretched, compressed or otherwise adjusted prior to, during, or after implantation.

The apparatuses may further comprise a wing. The wing may be attached to the arm of the apparatus in a variety of ways and may comprise a variety of connectors for attaching the wing to the arm as described above. The wing may further comprise an aperture configured to receive the arm of the apparatus. The point of attachment of the wing to the arm may vary. In some embodiments, the wing is attached to the arm near the midsection of the wing. Generally, the longitudinal axis of the wing is substantially perpendicular to the longitudinal axis of the arm.

When implanted, the placement of the wing relative to the spine may vary. In some embodiments, the wing is positioned at a posterior location. In some embodiments the wing is positioned to either side of the longitudinal axis of the spine. In some such embodiments, the wing is positioned to either side of the spinous processes located along the axis of the spine. In these embodiments, the wing may be positioned in the interlaminar space between adjacent vertebrae. Similarly, the orientation of the wing relative to the longitudinal axis of the spine may vary. In some embodiments the longitudinal axis of the wing is; substantially parallel to the longitudinal axis of the spine. In other embodiments, the wing is not aligned with the spine. These non-parallel orientations may serve to accommodate the various shapes and sizes of nearby vertebral components, many off which are not parallel to the spine.

The exact shape of the wing may vary. The wing may take a variety of forms, including, but not limited to a bar or a plate. In such embodiments, the outline of the wing may vary to accommodate the anatomical form or contour of nearby vertebrae. Similarly, the exact dimensions of the wing may vary. The desired length will, generally depend upon the desired placement of the wing within the spinal column. In some embodiments, the wing is short enough to fit within the interlaminar space between adjacent vertebrae in some embodiments, the wing is approximately the same length as the distance between the first and second supports of the apparatus. In some embodiments, the length of the wing is shorter than the distance between adjacent spinous processes. In other embodiments, the wing is long enough to span the distance between adjacent spinous processes. In any of these embodiments, the wing may serve to minimize the flexion, rotation, extension, lateral bending and translation of the spine by restraining the motion of the adjacent vertebrae as the vertebrae make contact with the wing as the spine moves. As described above the length and width of the wing will also depend upon such considerations as minimizing interference with other elements of the spine and ensuring the wing is easily implantable.

Each of the components of the medical apparatus may comprise, a variety of materials or combinations of materials. In some embodiments, the components, such as the body, supports, arm, sleeve, wing, and connectors, comprise a biologically compatibles material. A variety of biologically compatible materials may be used, including, but not limited to metals, such as titanium, titanium alloys, chrome cobalt or stainless steel. Other biocompatible materials include graphite and ceramics, such as hydroxyapatites. Plastics may also be employed. Suitable plastics include polyethylene (e.g. ultra high molecular weight polyethylene), polypropylene, polyether ester ketone, and silicones.

Although the embodiments described above make reference to two supports, the medical apparatuses of the present invention may include a plurality of supports. In some embodiments, the apparatuses comprise a third and fourth support. The third support is configured to accommodate a vertebral component of the second vertebra disposed above or below a third vertebra and the fourth support is configured to accommodate a vertebral component of the third vertebra. Similarly, the apparatuses may include a plurality of arms and wings. The characteristics of the additional supports, arms and wings may vary as described above.

The apparatuses disclosed herein may be used without fixing, attaching or otherwise securing the apparatus to the spine. In these embodiments, the apparatus may be held in place by the pressure of the vertebrae against the apparatus. In other embodiments, the apparatuses are secured to the spine. The apparatuses may be secured to the spine in a variety of ways. For example, any of the components of the apparatuses, including the body, the supports, the arm, and/or the wing may comprise a connector for securing the apparatus to the spine. A variety of connectors may be used, including but not limited screws, hooks or pins. Suitable screws and hooks include, but are not limited to, pedicle screws, polyaxial pedicle screws, lateral mass screws or polyaxial hooks and the like, such as those disclosed in U.S. Pat. Nos. 5,591,166; 5,628,740; 6,626,908; and in U.S. Patent Publication No. 2005/0113927. The connectors may attach to a variety of vertebral elements, including, but not limited to, pedicles, lamina or spinous processes. The apparatus may also include wires or bands in order to tie or hold the apparatus in place.

The figures show examples of medical apparatuses according various embodiments. The embodiments shown in the figures are intended only to exemplify the invention and should not be construed to limit the invention to any particular embodiment. The drawings are not necessarily to scale and the relative dimensions of the components of the apparatuses provided therein may deviate from those shown in the figures.

Figure 1B:
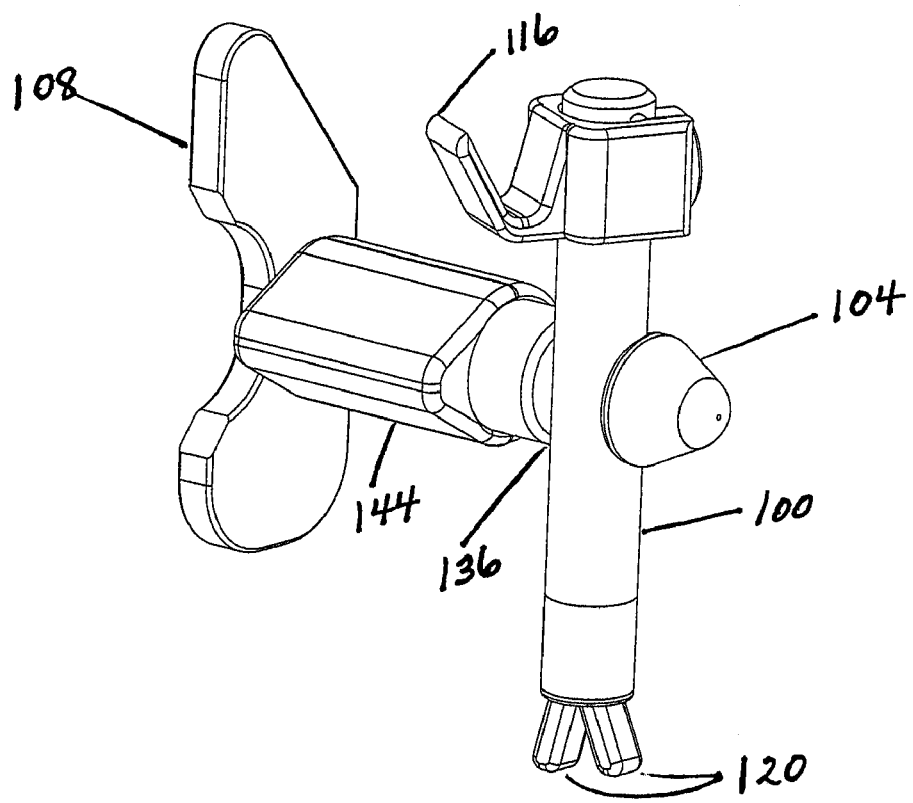
FIG. 1B is a rear view of the apparatus shown in FIG. 1A.

FIG. 1A depicts an apparatus comprising a body 100, an arm 104 and a wing 108. A rear view of the apparatus is shown in FIG. 1B. The longitudinal axes of the body, arm, and wing are labeled 110, 112, and 114, respectively. In this embodiment, the body is a rod and comprises two supports: a hook 1116 and two pegs 120 forming a, V-shape. A vertebral component of a first vertebra may rest in, and be supported by, the bend 124 formed by the hook. A connector 128 attaches the hook to one end of the body. In some embodiments, the book may be rotated around and translated along the longitudinal axis of the body prior to fixing its position on the body with the connector. Similarly, the vertex 132 formed by the pegs may be placed over a vertebral component of a second vertebra. In some embodiments, the V-shaped peg support is integrated into the body of the apparatus. By way of a non-limiting example, a plastic body having V-shaped peg support on one end may be formed by through an injection or extrusion molding process. In other embodiments; the V-shaped peg support is a distinct piece of hardware and comprises any of the connectors for attaching the support to the body described above.

The arm 104 extends substantially perpendicularly from the body 100. The arm comprises an aperture 136 through which the body may be inserted. The aperture shown in FIG. 1B is a slot, but in other embodiments, the aperture may bore through the arm 104. The arm also comprises a connector 140 for attaching the arm to the body. The arm may be rotated around and translated along the longitudinal axis of the body prior to fixing its position on the body with the connector. As shown in the figures, one end of the arm may be in the shape of a blunted cone. The arm further comprises a sleeve 144 disposed around the arm. As shown in FIG. 1B, the cross-section of the sleeve is in the shape of an egg. In some embodiments, the sleeve may be rotated around and translated along the longitudinal axis of the arm.

The wing 108 extends substantially perpendicularly from the end of the arm 104. The wing also comprises a connector 148 for attaching the wing to the arm. The wing may be rotated around the longitudinal axis of the arm prior to fixing its position on the arm with the connector. In the embodiment of FIGS. 1A and 1B, one end 150 of the wing is pointed and the other end 152 is rounded.

Figure 2:
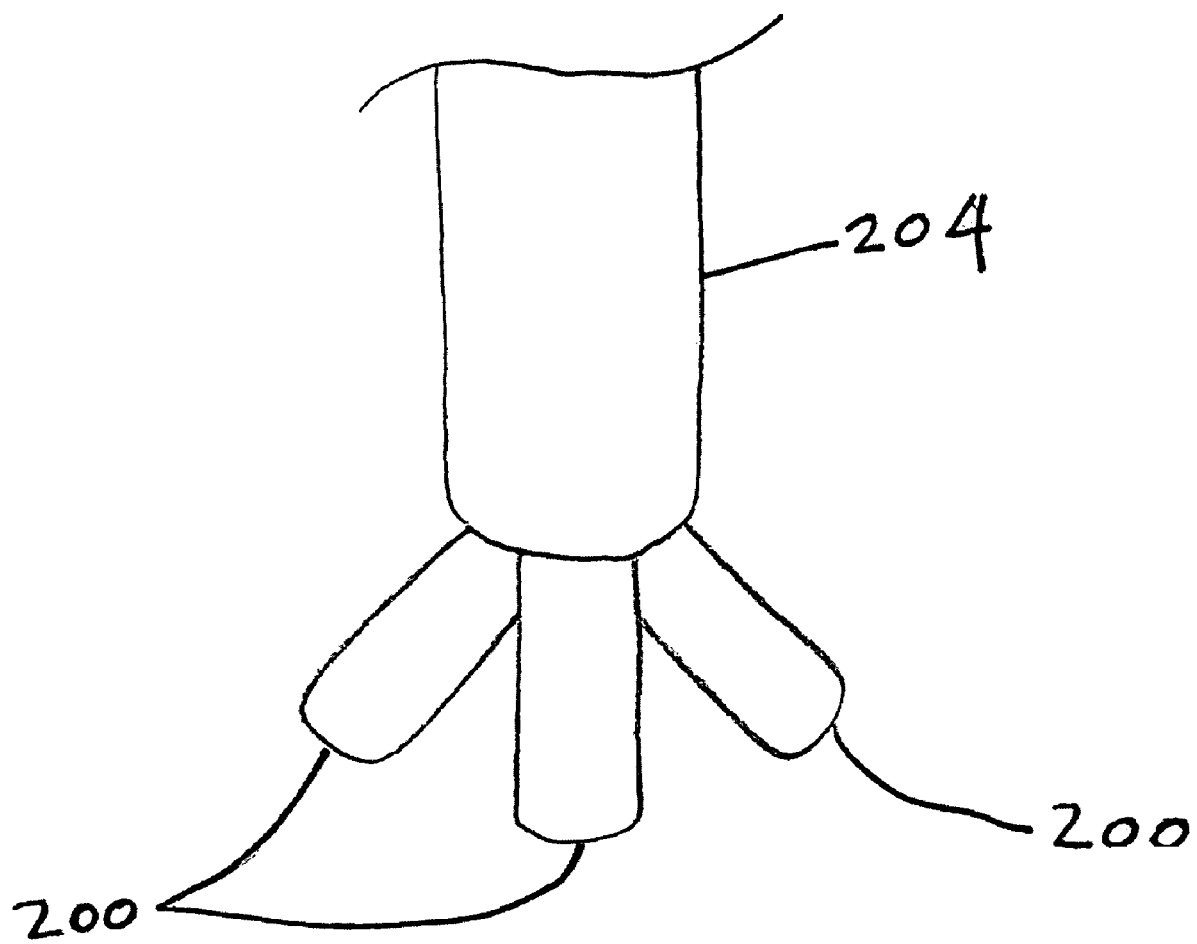
FIG. 2 shows an apparatus with three pegs according to another embodiment.

FIG. 2 shows a support configured to accommodate a vertebral component. The support comprises three pegs 200 extending from the end of the body 204 to form a tripod or claw shape.

Figure 3:
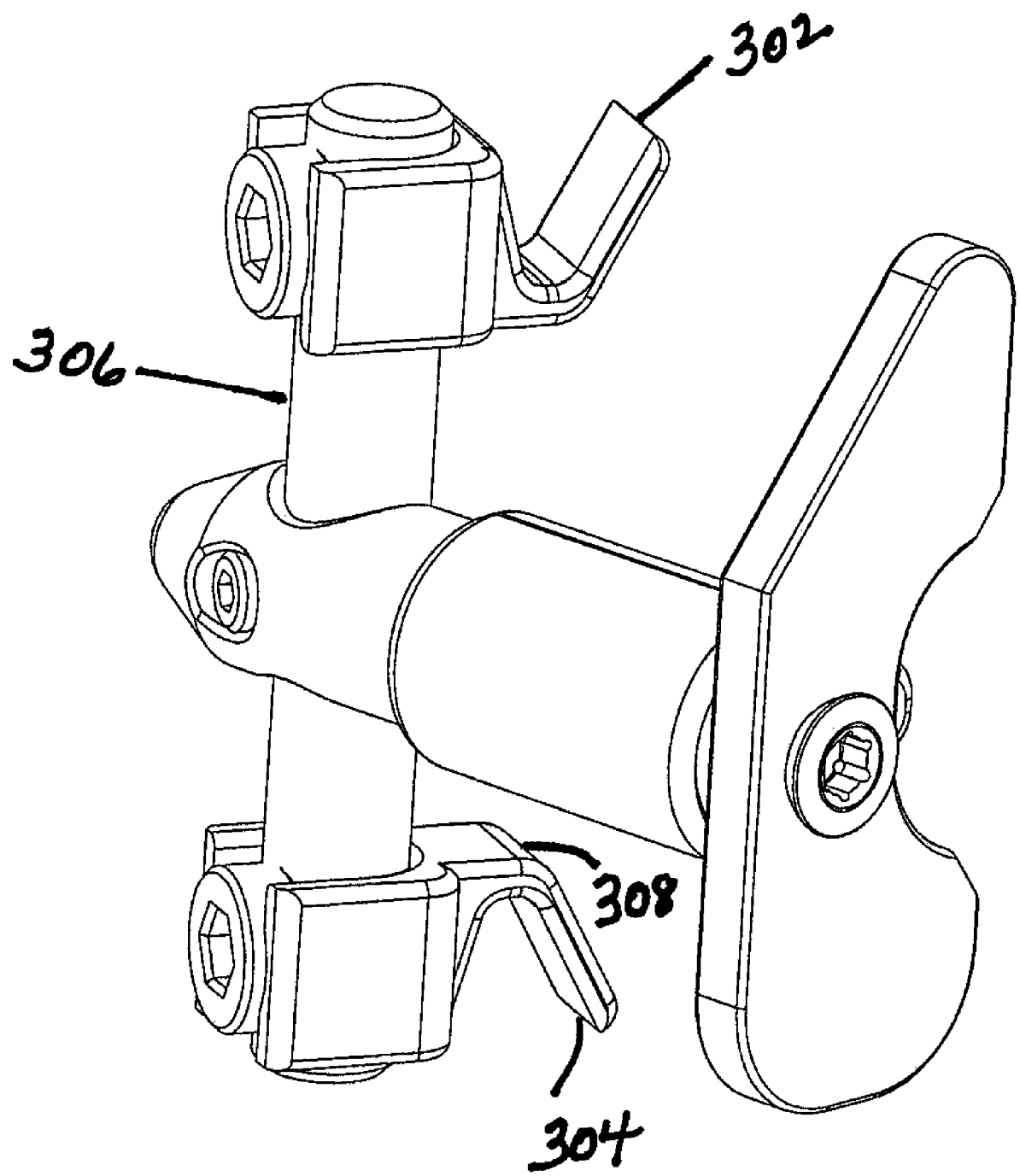
FIG. 3 is an illustration of an interlaminar hook apparatus according to one embodiment.

FIG. 3 shows another embodiment of an apparatus comprising two hooks 302 and 304 on opposite ends of the body 306. In this embodiment, the bend 308 formed in the hook 304 may be placed over a vertebral component of a second vertebra.

Figure 4:
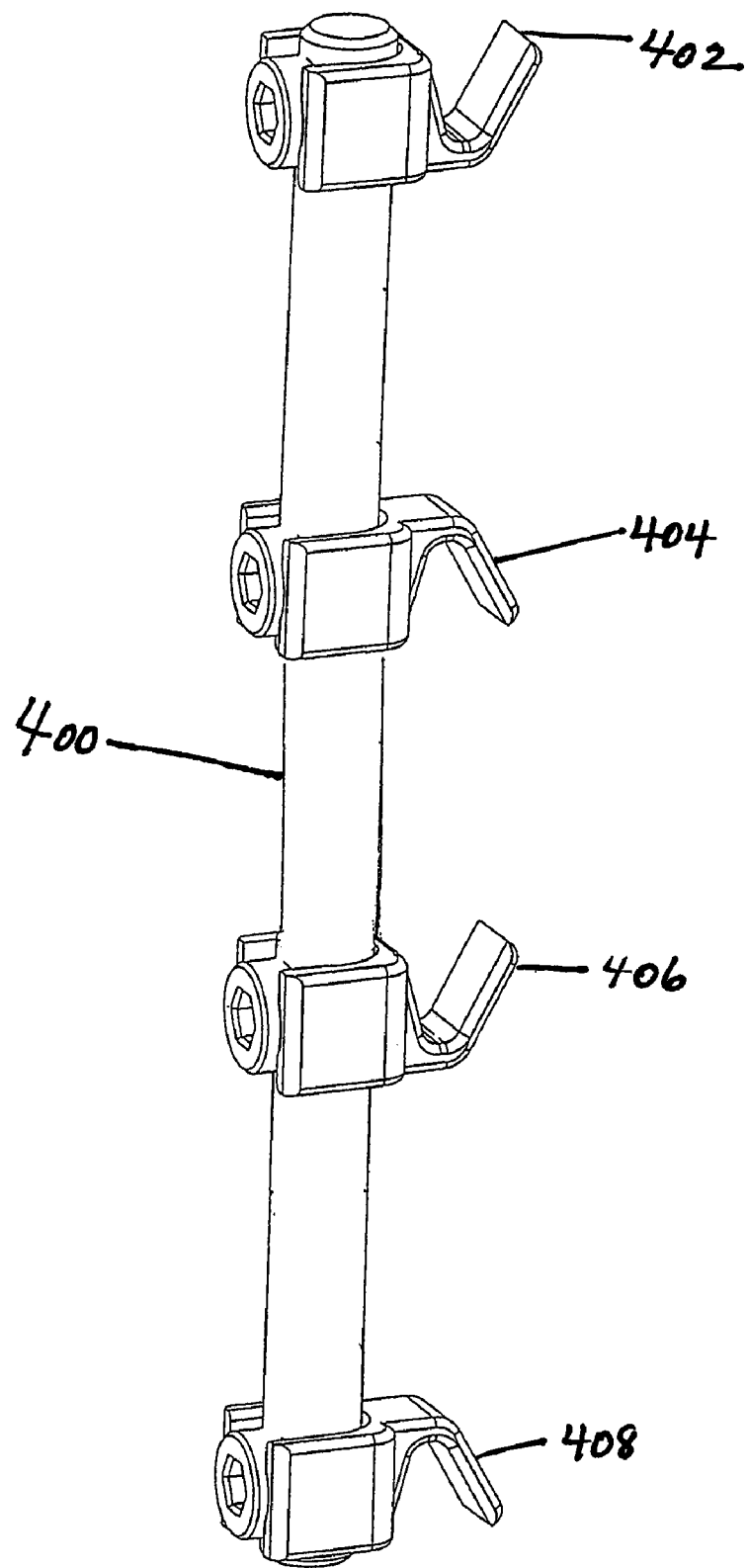
FIG. 4 depicts an interlaminar hook apparatus having multiple hooks disposed along the length of the apparatus according to one embodiment.

FIG. 4 shows another embodiment of an apparatus comprising four supports disposed along the length of the body 400 of the apparatus. A first hook 402 accommodates a vertebral component of a first vertebra. The second hook 404 and the third hook 406 accommodate different, vertebral components of a second vertebra disposed below the first vertebra. A fourth hook 408 accommodates a vertebral component of a third vertebra disposed below the second vertebra.

Figure 5:
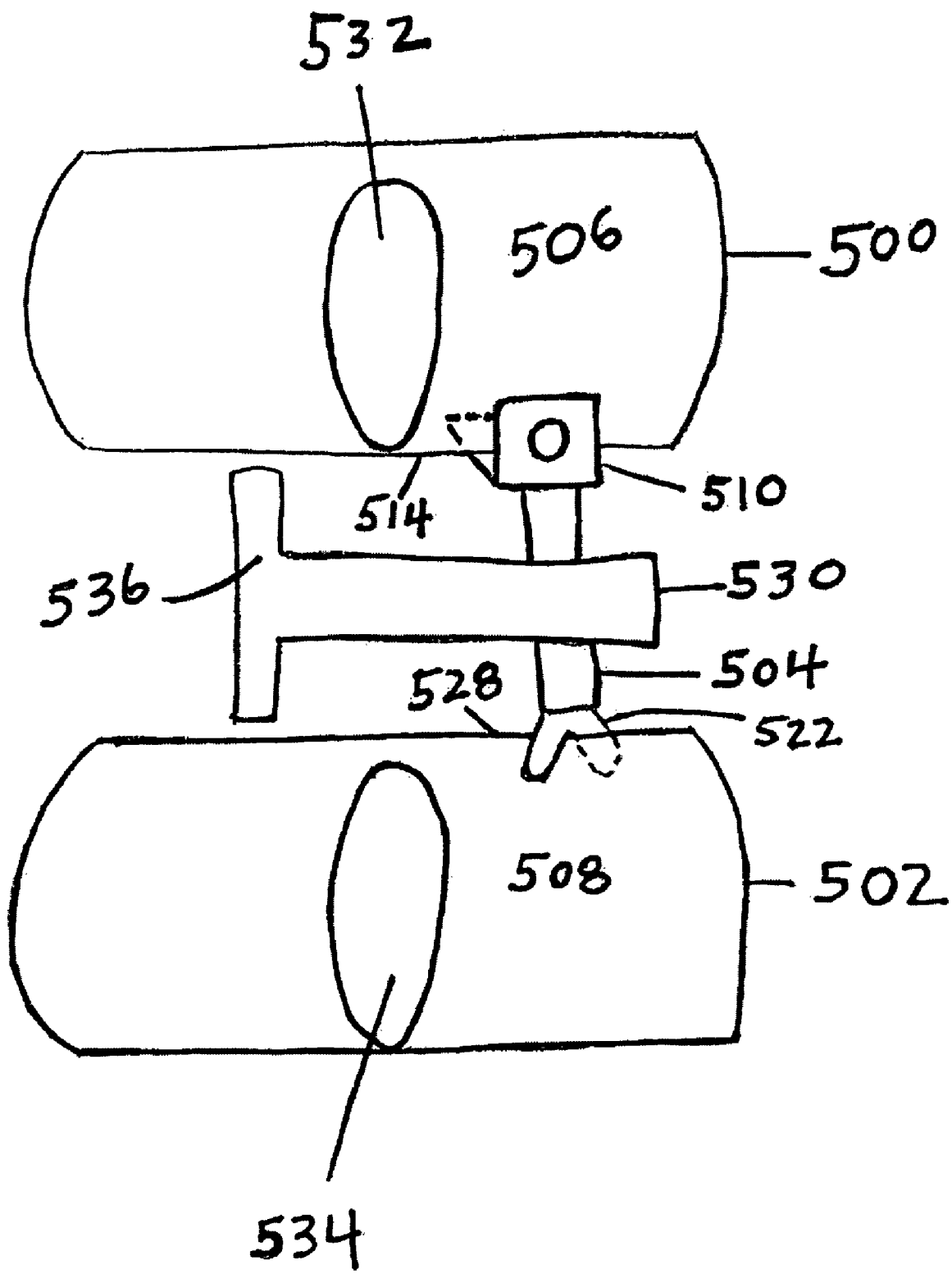
FIG. 5 illustrates one possible orientation of an interlaminar hook apparatus between vertebrae according to one embodiment.

FIG. 5 shows a posterior view of two adjacent vertebrae 500, 502 and an apparatus according to the present invention. The body 504 fits in the interlaminar space formed by the laminae 506, 508 of the vertebrae. The first support 510 is a hook. A portion of the inferior edge 514 of the lamina of the first vertebra rests in the bend formed by the hook. The portion of the hook shown in dotted lines extends towards the anterior of the vertebra 500. The second support 522 comprises two pegs forming a V-shape. The vertex formed by the pegs rests atop a portion of the superior edge 528 of the lamina of the second vertebra. The portion of the peg shown in dotted lines extends towards the anterior of the vertebra 502. Although the body 504 and supports 510, 522 are shown off to the side of the spinous processes 532, 534, in other embodiments, the body and supports may be positioned closer to the spinous processes. In such embodiments, the first support 510 may be placed where the lamina 506 merges with the spinous process 532 at the inferior aspect of the vertebra 500. The second support 522 may be placed where the lamina 508 merges with the spinous process 534 at the superior aspect of the vertebra 502.

As shown in FIG. 5, the arm 530 fits in the interspinous process space formed by the spinous processes 532, 534 of the first and second vertebrae, respectively. As described above, the width of the arm may be small enough to minimize contact with the adjacent spinous processes. In other embodiments, the width may be sufficient to contact, and aid distraction of, the spinous processes. The wing 536 fits in the interlaminar space to the left of the spinous processes. In some embodiments, the wing may be longer. The wing may be long enough to overlap with the lamina 506, 508 or even long enough to overlap with the spinous processes 532, 534. Although in some embodiments, the dimensions of the wing are sufficient to minimize contact with the laminae and spinous processes of the vertebrae 500, 502, in other embodiments, the wing may make contact with these vertebral components in order to restrain the motion of the adjacent vertebrae as described above.

In another aspect, methods of using the medical apparatuses are provided. The methods comprise implanting into a subject any of the medical apparatus disclosed herein. The apparatuses may be implanted by an open procedure, endoscopically or laprascopically. In some embodiments, the methods further comprise contacting the first support with at least a portion of the lamina of the first vertebra and contacting the second support with at least a portion of the lamina of the second vertebra. In other embodiments, the methods further comprise attaching the apparatus to the spine via a connector as described above. The implantation of the apparatuses may take place in stages and in various sequences. By way of a non-limiting example for those embodiments in which the apparatus includes a body, an arm, and a wing, the arm, by itself, may be inserted between the spinous processes of adjacent vertebrae. Next, the body may be connected to the implanted arm. Finally, the wing may be connected to the implanted arm.

In some embodiments, the method further comprises distracting the first and second vertebrae prior to completing the implantation of the apparatus. Any of the tools and methods known to those skilled in the art may be used to distract the vertebrae. By way of a non-limiting example, adjacent vertebrae may be distracted by forcing apart the spinous processes on the adjacent vertebrae. In some embodiments, the components of the apparatuses disclosed herein may be used to achieve the distraction. For example, the arm of the apparatus may be inserted into the space between adjacent spinous processes. The width of the arm itself may be sufficient to contact and force apart the spinous processes. Alternatively, the arm may be urged upward or downward so as to spread apart the spinous processes. If the cross-section of the arm is an ellipse or an egg, the arm may be rotated to bring the major axis of the ellipse or egg in line with the spine, thereby spreading apart the spinous processes.

In still other embodiments, the methods further comprise forming a notch in a vertebral component of the first vertebra or the second vertebra or both. The notch is configured to accommodate any of the supports disclosed herein. Any of the tools and methods known to those skilled in the art may be used to form the notch. The notch may serve to prevent the supports from slipping out of place while the spine, moves. In some embodiments, the notch is formed in either or both laminae of the first and second vertebrae. In such embodiments, the notch may be formed on the superior edge or inferior edge of the laminae.

The inventions illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

Thus, it should be understood that although the present invention has been specifically disclosed by preferred embodiments and optional features, modification, improvement and variation of the inventions herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

For the purposes of this disclosure and unless otherwise specified, "a" or "an" means "one or more." All patents, applications, references and publications cited herein are incorporated by reference in their entirety to the same extent as if they were individually incorporated by reference.

While some detailed embodiments have been illustrated and described, it should be understood that such detailed embodiments are merely exemplary and changes and modifications can be made therein in accordance with ordinary skill in the art without departing from the invention in its broader aspects as defined, in the following claims.

The invention claimed is:

1. A medical apparatus comprising a body having a length, the body comprising:
   a first support disposed along the length of the body, the first support configured to accommodate at least a portion of a lamina of a first vertebra disposed above or below a second vertebra;
   a second support disposed along the length of the body, the second support configured to accommodate at least a portion of a lamina of the second vertebra; and
   an arm having an aperture adapted to receive the body so that the arm extends from, and substantially perpendicular to, the body;
   wherein the first and second supports are configured to increase the space between the first vertebra and the second vertebra.

2. The medical apparatus of claim 1, wherein the first support and second support are configured to accommodate at least a portion of the superior edge or the inferior edge of the lamina.

3. The medical apparatus of claim 1, wherein the first support comprises a hook.

4. The medical apparatus of claim 1, wherein the first support comprises a hook and the second support comprises a hook.

5. The medical apparatus of claim 1, wherein the second support comprises at least two pegs extending from an end of the body to form a V-shape.

6. The medical apparatus of claim 5, wherein the second support comprises three pegs extending from an end of the body to form a tripod shape.

7. The medical apparatus of claim 1, further comprising a wing extending from the arm.

8. A medical apparatus comprising a body having a length, the body comprising:
   a first support disposed along the length of the body, the first support configured to accommodate at least a portion of a lamina of a first vertebra disposed above or below a second vertebra;
   a second support disposed along the length of the body, the second support configured to accommodate at least a portion of a lamina of the second vertebra; and
   an arm extending from and substantially perpendicular to the body, the arm comprising a sleeve having a cross-section in the shape of an ellipse or an egg;
   wherein the first and second supports are configured to increase the space between the first vertebra and the second vertebra.

9. The medical apparatus of claim 8, wherein the first support comprises a hook and the second support comprises at least two pegs extending from an end of the body to form a V-shape.

10. The medical apparatus of claim 8, further comprising a wing extending from the arm.

11. A medical apparatus comprising a body having a length, the body comprising:
   a first support disposed along the length of the body, the first support configured to accommodate at least a portion of a lamina of a first vertebra disposed above or below a second vertebra; and
   a second support disposed along the length of the body, the second support comprising three pegs extending from an end of the body to form a tripod shape and configured to accommodate at least a portion of a lamina of the second vertebra;
   wherein the first and second supports are configured to increase the space between the first vertebra and the second vertebra.

12. The medical apparatus of claim 11, further comprising an arm extending from, and substantially perpendicular to, the body.

13. The medical apparatus of claim 12, wherein the arm comprises an aperture adapted to receive the body.

14. The medical apparatus of claim 12, wherein the arm comprises a sleeve having a cross-section.

15. The medical apparatus of claim 14, wherein the cross-section of the sleeve is in the shape of an ellipse or an egg.

16. The medical apparatus of claim 12, further comprising a wing extending from, and substantially perpendicular to, the arm.

17. The medical apparatus of claim 11, wherein the body, the first support and the second support comprise a biologically compatible material selected from the group consisting of titanium, a titanium alloy, stainless steel, and a polymer.

18. The medical apparatus of claim 11, wherein the first support and second support are configured to accommodate at least a portion of the superior edge or the inferior edge of the lamina.

19. The medical apparatus of claim 11, wherein the first support is a hook.

20. A method comprising:
    implanting into a subject a medical apparatus comprising a body having a length, the body comprising:
        a first support disposed along the length of the body, the first support configured to accommodate at least a portion of a lamina of a first vertebra disposed above or below a second vertebra;
        a second support disposed along the length of the body, the second support configured to accommodate at least a portion of a lamina of the second vertebra;
        wherein the first and second supports are configured to increase the space between the first vertebra and the second vertebra;
    connecting an arm to the body so that the arm extends substantially perpendicular to the body, the arm having a wing extending substantially parallel to the arm.

21. The method of claim 20, further comprising contacting the first support to at least a portion of the lamina of the first vertebra and contacting the second support to at least a portion of the lamina of the second vertebra.

22. The method of claim 20, further comprising distracting the first and second vertebrae prior to completion of implantation.

23. The method of claim 20, further comprising forming a notch in the lamina of the first vertebra or in the lamina of the second vertebra or both, wherein the notch is configured to accommodate the first support or the second support.

24. The method of claim 20, wherein the first support is a hook and the second support comprises at least two pegs extending from an end of the body to form a V-shape.

25. The method of claim 20, further comprising implanting the apparatus by inserting the arm between the spinous process of the first vertebra and the spinous process of the second vertebra, connecting the body to the arm, and connecting the wing to the arm.

26. A medical apparatus comprising a body having an length extending along an axis, the body comprising:
    a first support coupled to the body, the first support configured to accommodate at least a portion of a lamina of a first vertebra;
    a second support coupled to the body and axially aligned with the first support, the second support configured to accommodate at least a portion of a lamina of a second vertebra;
    a third support coupled to the body and axially aligned with the first and second supports, the third support configured to accommodate at least a portion of a lamina of a third vertebra;
    wherein the supports comprise a hook.

27. The medical apparatus of claim 26, further comprising a fourth support coupled to the body and axially aligned with the first, second and third supports, the fourth support configured to accommodate at least a portion of a lamina of a fourth vertebra.

* * * * *